United States Patent
Suarez et al.

(10) Patent No.: US 9,592,371 B2
(45) Date of Patent: Mar. 14, 2017

(54) IMPLANTED IV PORT PROTECTION DEVICE

(71) Applicants: William Suarez, Pendleton, IN (US); Heather Suarez, Pendleton, IN (US)

(72) Inventors: William Suarez, Pendleton, IN (US); Heather Suarez, Pendleton, IN (US)

(*) Notice: Subject to any disclaimer, the term of this patent is extended or adjusted under 35 U.S.C. 154(b) by 338 days.

(21) Appl. No.: 13/846,968

(22) Filed: Mar. 19, 2013

(65) Prior Publication Data

US 2014/0283850 A1  Sep. 25, 2014

(51) Int. Cl.
*A61F 13/00* (2006.01)
*A61M 39/02* (2006.01)

(52) U.S. Cl.
CPC .... *A61M 39/0208* (2013.01); *A61M 39/0247* (2013.01); *A61M 2039/0288* (2013.01)

(58) Field of Classification Search
CPC ...... A61K 9/00; A61B 6/0442; A61B 5/0452; A61B 5/0456; A61B 5/042; A61B 17/3403; A61B 19/5212; A61B 19/5244; A61B 19/54; A61B 2017/00274; A61B 2017/3413; A61B 2018/00547; A61B 2019/542
USPC .................. 128/878–879, 888–889
See application file for complete search history.

(56) References Cited

U.S. PATENT DOCUMENTS

| | | | |
|---|---|---|---|
| 4,317,237 A | | 3/1982 | Porte |
| 4,846,807 A | * | 7/1989 | Safadago ...................... 604/179 |
| 5,238,010 A | * | 8/1993 | Grabenkort et al. ......... 128/888 |
| 5,245,706 A | | 9/1993 | Moschetti et al. |
| 5,621,914 A | | 4/1997 | Ramone et al. |
| 5,897,519 A | * | 4/1999 | Shesol .................. A61M 25/02 602/75 |
| 6,576,808 B1 | | 6/2003 | Dreyer |
| 6,827,707 B2 | * | 12/2004 | Wright et al. ................ 604/180 |
| 8,197,447 B2 | * | 6/2012 | Wright .......................... 604/174 |
| 8,220,079 B2 | | 7/2012 | Syska et al. |
| 8,269,059 B2 | * | 9/2012 | Wright et al. .................. 602/54 |
| 2009/0126087 A1 | | 5/2009 | Armstrong et al. |
| 2014/0031757 A1 | * | 1/2014 | Rozier .................. A61M 25/02 604/179 |

* cited by examiner

*Primary Examiner* — Michael Brown
(74) *Attorney, Agent, or Firm* — John DRitchison; Ritchison Law Offices, PC

(57) ABSTRACT

A port protection device mainly comprised of a rigid back plate with a shock absorbing pad adhered underneath, the device being held in place against the chest of the child by using elastic straps and latching clasps. The absorbing pad provides a consistent soft contact area with the skin and chest which distributes the impact over a large area rather than localized points. This distribution reduces the possibility of pain and injury to the chest. The adjustable elastic straps allow the device be held tightly against the body and chest and not allow for movement of the device during sports and physical activity.

13 Claims, 10 Drawing Sheets

FRONT

FIGURE 1 - FRONT

FIGURE 8 - BACK

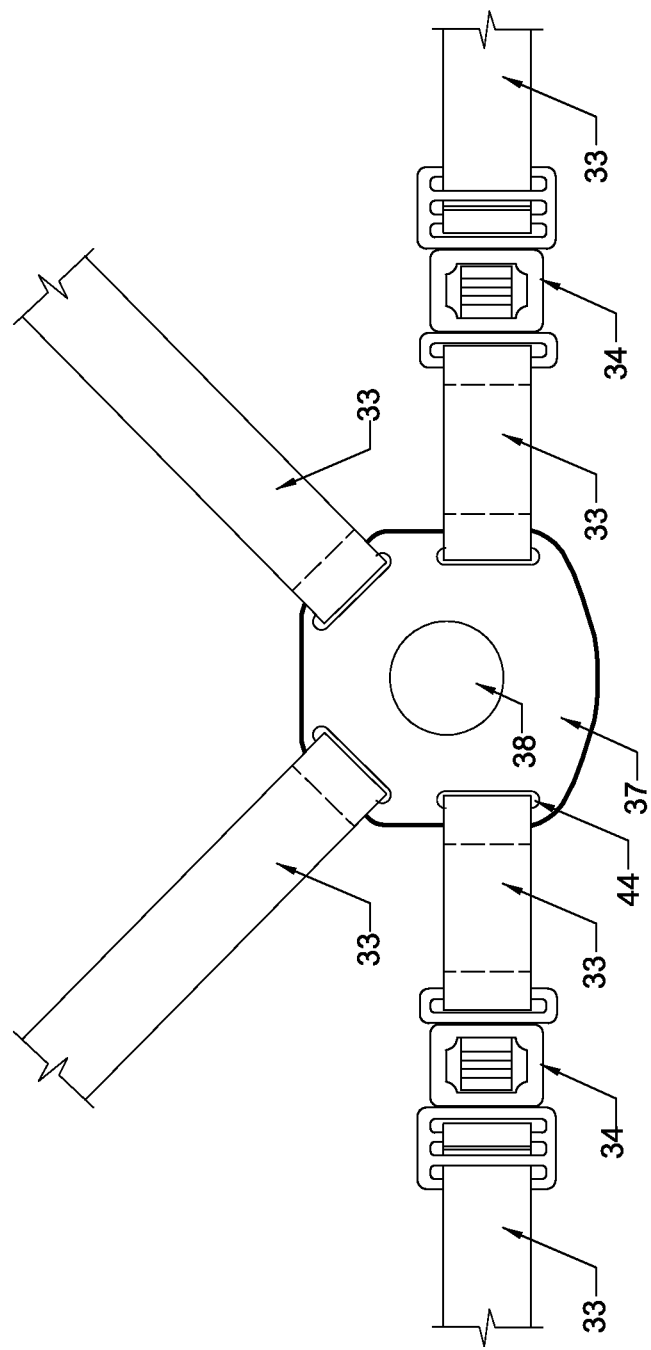

IMPLANTED IV PORT PROTECTION DEVICE

CROSS-REFERENCE TO RELATED APPLICATIONS

None.

FIELD OF INVENTION

The present invention relates to a device designed for protecting the surrounding area where a surgically implanted port or medical "portacath" device is located. The Port Protection Device would protect the chest and port from damage or injury during daily physical activities and sports. It would be capable of being placed over different areas on the upper or lower chest depending on the placement of the port. More specifically, the present invention relates to protective apparatus suitable to provide users of port protection devices from impacts due to applied or external forces.

FEDERALLY SPONSORED RESEARCH

None.

SEQUENCE LISTING OR PROGRAM

None.

BACKGROUND

Field of Invention and Prior Art

A. Problem Addressed

As far as known, there are no special port protection devices in prior art like this one shown herein. It is believed that this product is unique in its design and technologies. The solution is driven primarily to aid children who use surgically implanted port devices and struggle with fear of getting hurt due to contact or impact to that area. Many of these children are capable of playing sports and desire to participate but they run the risk of injury to the area during the activity.

The port protector allows children, adolescents and adults to live normal lives and participate in physical activities. The children may participate in gym classes, playing with friends, or engaging in sports. Children with implanted ports tend to refrain from sports and strenuous physical activity due to the potential impact to the port area. There is chance of significant pain involved with impact as well as simply an object touching the port. A common condition children with implanted ports are experiencing is called "port walk", where a child deliberately walks hunched over in an attempt to "protect the port and port area" from impact or touch resulting in pain. One notes that the use with children is fully anticipated but is not a limitation. Adolescents and adults may also benefit from the new device. They too may participate in physical activities, exercise and sporting events with the knowledge that the port and surrounding area is protected from impacts.

The port protector would be manufactured in standard off-the-shelf sizes and not need to be custom made for individual users. The early prototypes have focused primarily on the needs of children, but the concept extends as well for others as previously stated above.

B. Prior Art

Prior Art for similar devices are limited since this is a relative unique device. A chest protector was taught by Moschetti, et al in a U.S. Pat. No. 5,245,706 issued in 1993. It shows a protective device for the chest for use in athletic activities such as baseball, softball and hockey. It is a sternum pad made of heavier materials and held by straps. It does not have the absorption materials or configuration of the present port protector nor can it be placed in various locations over the portacath. Another protective garment device is demonstrated in U.S. Pat. No. 5,621,914 issued to Ramone et al in 1997. Here is taught a shirt device without the straps, location manner, or absorption pad stressed by the Suarez port protector.

An Apparatus and method to protect an implanted medical device or wound was provided in the U.S. Pat. No. 6,576,808 as a US patent issued to Dreyer in 2003. Dreyer describes a soft donut shaped pad intended to be used in a vehicle. It does not function or anticipate the instant port protector since it has no transportability with the user during physical activities. A U.S. Pat. No. 8,220,079 issued to Syska et el in 2012 showed a device called a "Portacath Protection Device". It has three points of contact that would be adhered or attached to a protective shirt worn by the port user. This device does not show the adjustability and focused/specific use as demonstrated in the Suarez protective device.

A US Patent Application Publication No. 2009/0126087 by Armstrong et al shows an apparatus for protecting a pacemaker. It shows a raised dome but little ability to cover the chest area with straps directly over the portacath. It again uses a tee shirt for a medium to wear the device by the user. It lacks the function and fit of the Suarez port protector. Finally, heavier and bulky chest protectors have been shown for various sports, but the lack the specific location and lightweight feature of the present invention. One such example is the chest protector shown in U.S. Pat. No. 4,317,237 issued to Porte in 1982. Such devices as these lack the effectiveness of the new Suarez device.

BACKGROUND OF THE INVENTION

Persons undergoing intensive medical treatment may be required to have repeated and recurring medical infusion of drugs and hormones, or multiple drawing of blood samples. To ease patient discomfort associated with repeated needle sticks, the patient may elect to have a port surgically implanted beneath the skin. Medical conditions requiring frequent extended intravenous infusion that use ports include but are not limited to Cancer, Hemophilia, CVID, and Cystic Fibrosis, among others. Another device commonly used for frequent infusions is a PICC-Line (peripherally inserted central catheter). This too may be protected within the spirit and scope of the innovation presented here.

Various types of ports are currently available from manufacturers such as Porta-Cath, Microport, Bardport, PowerPort (power injectable), Passport, Infuse-a-Port, Medi-Port, and Lifesite (for hemodialysis patients) from companies including Bard Access Systems, Navilyst Medical, Smiths Medical, MedComp, Rita Medical Systems and AngioDynamics. As more companies and variations of the implants evolve, this instant Port Protection Device may be easily adapted within the scope of the configuration and materials of the device presented herein to be used with the new port implants.

In medicine, a port (or portacath) is a small medical appliance that is installed beneath the skin.

A catheter connects the port to a vein. Under the skin, the port has a septum through which drugs can be injected and blood samples can be drawn many times, usually with less discomfort for the patient than a more typical "needle stick". A port consists of a reservoir compartment (the portal) that has a silicone bubble for needle insertion (the septum), with an attached plastic tube (the catheter). The device is surgically inserted under the skin in the upper chest or in the arm and appears as a bump under the skin. It requires no special maintenance and is completely internal so swimming and bathing are not a problem. The catheter runs from the portal and is surgically inserted into a vein (usually the jugular vein, subclavian vein, or superior vena cava). Ideally, the catheter terminates in the superior vena cava, just upstream of the right atrium. This position allows infused agents to be spread throughout the body quickly and efficiently. (Reference Wikipedia).

Ports often have many different uses, such as parenteral nutrition, delivery of chemotherapy, delivery of coagulation factors, withdrawal of blood from patients requiring frequent blood tests, delivery of antibiotics, and delivery of medications. Since the port is surgically implanted under the skin, there is a risk that the persons having such a port may damage it during the course of daily physical activities, especially for sports activities and the like. During such physical activities, people who have a port sometimes experience pain when physical contact is made with their port. Persons with a port are at a risk of rupturing the structural sutures that hold the port in place. It is also possible that the catheter may be ruptured or torn loose.

SUMMARY OF THE INVENTION

The device is a port protection device. The device is mainly comprised of a plastic back plate with a silicone pad adhered underneath which is held in place against the chest of the child by using elastic straps and latching clasps. The silicone pad provides a consistent soft contact area with the skin and chest which distributes the impact over a large area, instead of a few localized points. This would reduce the possibility of pain or injury to the chest. The use of adjustable elastic straps with clasps allow the device be set tightly against the body and chest and not allow for movement of the device during sports and physical activity.

OBJECTS AND ADVANTAGES

There are several objects and advantages of the Port Protection Device. These advantages and benefits are listed below.

TABLE A

| Item | Object/Advantage |
|---|---|
| 1 | Protect the child or user |
| 2 | Protect the implanted device |
| 3 | Promote confidence of the user in physical activity |
| 4 | Is light and durable |
| 5 | Is easy to clean |
| 6 | Is simple to attach around the body/chest of the child or user and requires no special tools |
| 7 | Is available in universal sizes and requires no special customization to the user |
| 8 | Is comprised of readily available materials |

Finally, other advantages and additional features of the present port protection device will be more apparent from the accompanying drawings and from the full description of the device. For one skilled in the art of medical and sporting protection devices and the like, it is readily understood that the features shown in the examples with this product are readily adapted to other types of protective devices for ports and other medical systems and devices.

BRIEF DESCRIPTION OF THE DRAWINGS

The accompanying drawings, which are incorporated in and constitute a part of this specification, illustrate an embodiment of the Port Protection Devices that are preferred. The drawings together with the summary description given above and a detailed description given below serve to explain the principles of the Port Protection Device. It is understood, however, device is not limited to only the precise arrangements and instrumentalities shown.

FIG. 12 is a front view with an embodiment showing front clasps for use with the device.

DESCRIPTION OF THE DRAWINGS—REFERENCE NUMERALS

Figure 1:
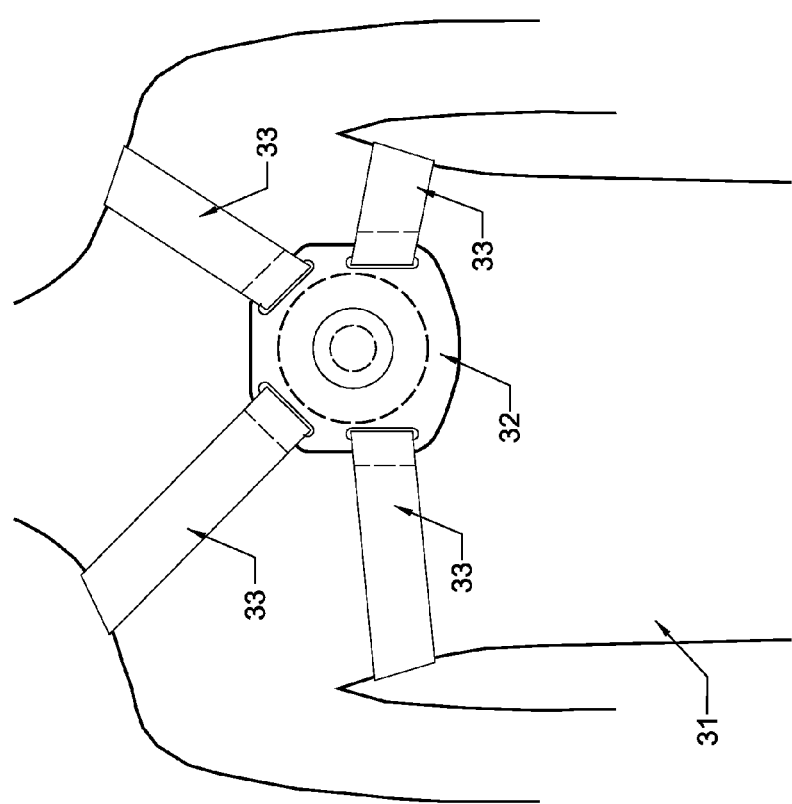
FIG. 1 is a front view of the present invention in use.

The following list refers to the drawings:

TABLE B

Reference numbers

| Ref # | Description |
|---|---|
| 31 | User/individual with the port |
| 32 | Port shield device |
| 33 | Means for securing such as a number of (elastic) straps |
| 34 | Means for securing and adjusting length of the strap 33 such as clasps, hooks, hook and loop devices [Velcro ™) or equal |
| 35 | Skin surface of individual 31 |
| 36 | Implanted Portacath device |
| 37 | Rigid back plate (still with resilience and pliable) |
| 38 | Dome raised above the general surface of the device |
| 39 | Pad-absorption material able to resist impact and cushion force of impact |
| 40 | Cut out, hole, or recess |
| 41 | Top surface of fabric |
| 41A | Bottom surface of fabric 41 |
| 41B | Top surface of fabric 41 |

TABLE B-continued

Reference numbers

| Ref # | Description |
|---|---|
| 42 | Means for securing, such as an adhesive placed in the inherent small gap between the top surface of the pad 37 and the lower surface of the back plate 39 |
| 43 | Apertures for venting |
| 44 | Slots in back plate 39 for straps 33 |
| 45 | PICC Line (not shown) |
| 46 | Sports bra (cross) razor back type strap |
| 47 | Single solid component (assembly or integral combination of pad 37 and plate 39 combination) |
| 48 | Hollow celled component (assembly or integral combination of pad 37 and plate 39 combination) |

DETAILED DESCRIPTION OF THE INVENTION

The present development is a port protection device. Particularly this new idea and concept is a product that is related to a device designed for protecting the surrounding area where a surgically implanted port is located. The Port Protection Device would protect the chest and port from damage or injury during daily physical activities and sports. It would be capable of being placed over different areas on the upper or lower chest, and/or abdomen depending on the placement of the port.

The preferred embodiment is a port protection device essentially comprised of a rigid back plate with a top and lower surface; a pad made of resilient material with a top surface and a lower surface, the top surface of the pad contiguously placed next to the lower surface of the back plate with a small gap at the junction of the contiguous surfaces and the lower surface of the pad next to a skin of a user; a means to secure the lower surface of the back plate to the top surface of the pad; a plurality of straps with a length long enough and able to wrap around a chest of the child; and a means to attach the plurality of straps to the back plate wherein the device is placed on the skin of the child directly over the port.

There is shown in FIGS. 1-12 a complete description and operative embodiment of the Port Protection Device. In the drawings and illustrations, one notes that the Figures demonstrate the general configuration and use of this product. The various example uses are in the operation and use section, below.

The foregoing and other features of the present Port Protection Device will be more readily apparent from the following detailed description and drawings of the illustrative embodiments of the invention in which various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

Figure 2:
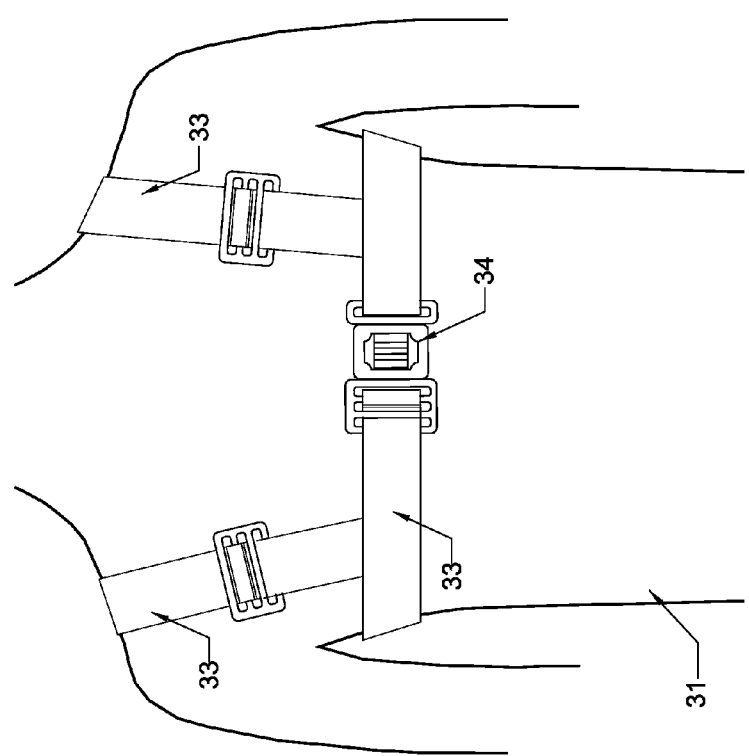
FIG. 2 is a back view of the present invention in use.
Figure 3:
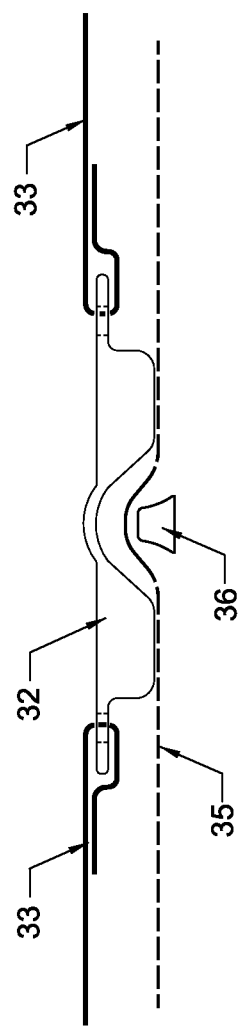
FIG. 3 is a cross section view of the present invention in use.

The port shield device 32 is shown in FIGS. 1 through 12. FIG. 1 shows a front view of a user 31 wearing the device 32 on his chest directly over the implanted Portacath device 36 or the like. The unit is held in place with means for securing such as a number of straps 33. FIG. 2 shows one configuration of the straps 33 and clasps 34 on the back of a user 31. These clasps 34 are one example of a means for securing and adjusting length of the strap 33 such as clasps, hooks, hook and loop devices [Velcro™], bra type clasps, or equal. Here the clasps 34 are along the back of the user. FIG. 3 shows a cross section of the device located on a subject which shows how the protection device 31 is placed on the skin 35 of the user 31 directly over the implanted port device 36 or PICC Line 45. Straps 33 hold the device 31 securely in place against the chest or abdomen of the user 31.

Figure 4:
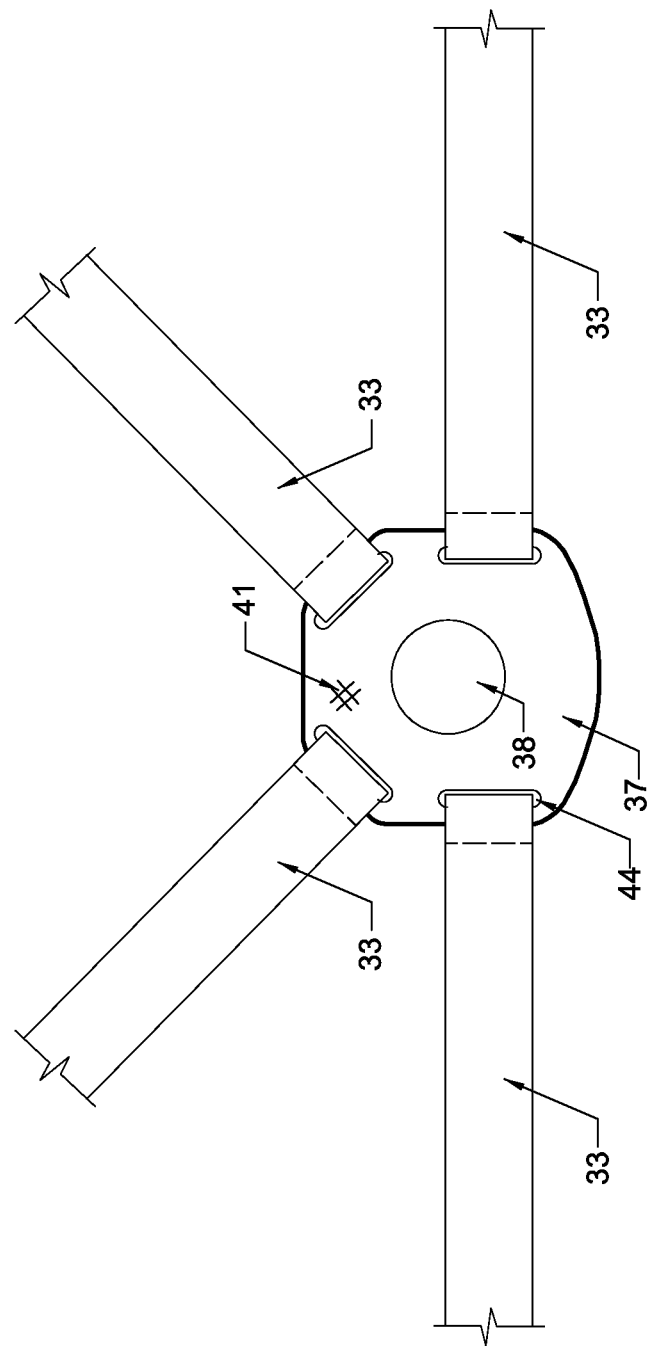
FIG. 4 is a front view of one embodiment of the present invention.
Figure 5:
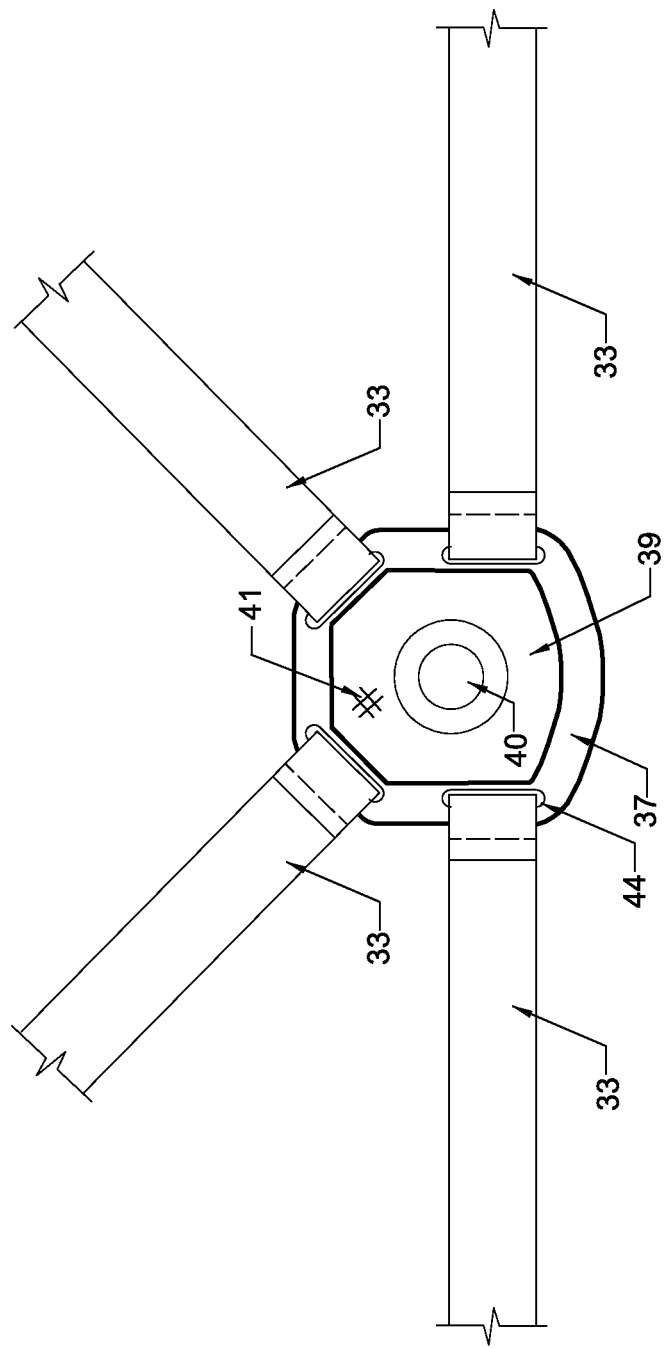
FIG. 5 is a rear view of one embodiment of the present invention.
Figure 6:
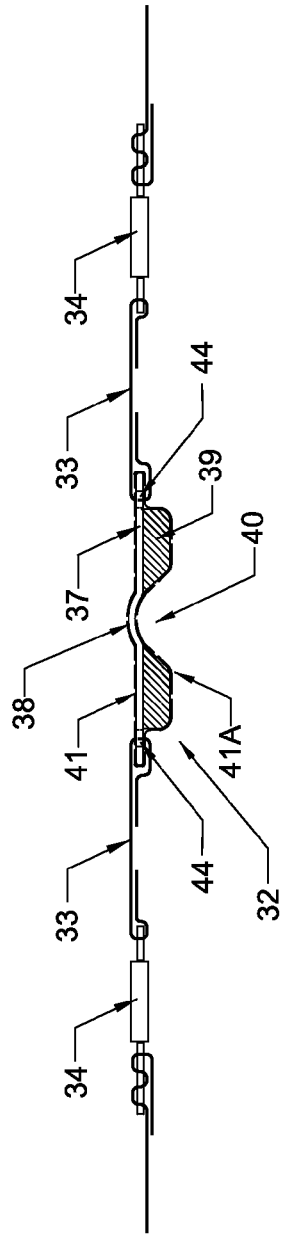
FIG. 6 is a cross section view of one embodiment of the present invention.
Figure 6A:
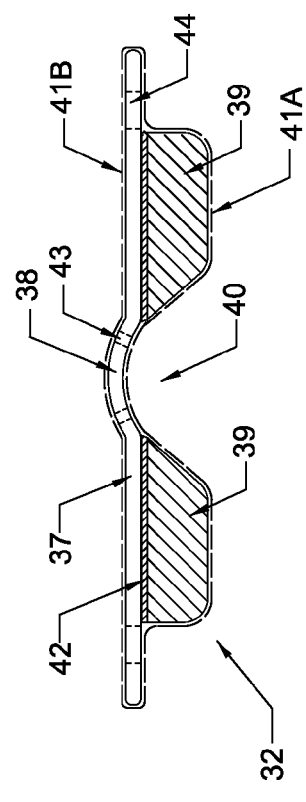
FIG. 6A is an enlarged cross sectional view of one embodiment of the present invention.
Figure 7:
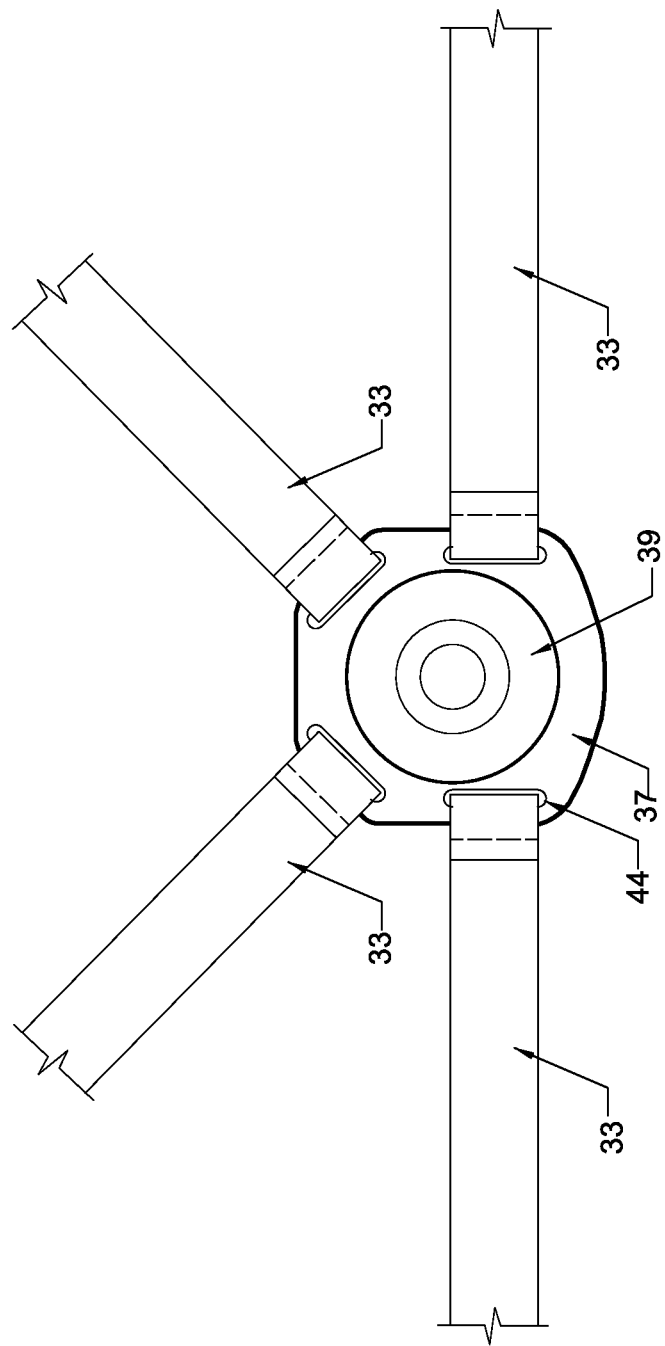
FIG. 7 is a back view of a second embodiment of the invention.

One embodiment of the device shown in FIGS. 4 through 6 and enlarged FIG. 6A consists of a pad 39 adhered to a rigid back plate 37. There would be a plurality of slots 44 cut into the back plate 37. The entire device 32 is covered in an encasing adhesive fabric 41. A plurality of straps 33 would be threaded through the slots 44 cut into the back plate 37. The device is placed directly on the skin 35 and held in place by the elastic straps 33. Clasps 34 attached to the straps 33 would allow adjustability to ensure a tight fight against the body 31 and prohibit movement or slippage of the device 32. The overall dimensions of the protective device, excluding the straps, are nominally or approximately 4 inches wide by 5 inches high, by 12 millimeters thick. This is exemplary and not a limitation of the size or configuration. Other shapes and sizes are possible.

The back plate 37 may be formed of polyethylene plastic. It would be between 1 millimeter and 5 millimeters thick. Preferably the back plate 37 will be a resilient/pliable material that is capable of slight deflection on impact to as to absorb and diminish any force of the impact. Other materials may be used, but polyethylene plastic would be preferred for rigid yet pliable characteristics. The rigid, pliable material here might also include—for example and not as a limitation—other materials such as molded plastic, rigid urethane, nylon, sheet plastic, rigid pressed cardboard, thin gaged (meaning less than 10 gage) metal, and composite material. In addition, a slightly raised dome 38 would be formed into the back plate 37 to allow for the port to extent into it in the event of a frontal impact. The dome 38 would have a base diameter approximately a nominal ⅝ of an inch and a height of approximately 3/32 of an inch. There may be holes or apertures 43 drilled into the back plate 37 and dome 38 to allow for venting. (See also FIG. 11).

The pad 39 which is attached to the underside of the back plate 37 may be made of a material with a means for securing 42 such as a silicone with adhesive backing 42. The pad 37 would have a top surface contiguous and positioned flatly against the lower surface of the back plate 39. There would be an inherent small gap naturally between the top surface of the pad 37 and the bottom surface of the back plate 39 where the means for securing 42 would be placed. The pad 39 would have a thickness between approximately 5 millimeters and 15 millimeters. Silicone is the preferred material for the pad 39 as it does not pack-out and it maintains the same thickness on impact. Another option for the pad 39 might be foam, such as Poron® urethane or the like, as it is lighter than the silicone. The shock absorbing material may also anticipate foam (open or closed cell), other urethanes, nylon, natural rubber, synthetic rubber, composite material, in addition to the general foam, Poron® urethane, and silicone gel mentioned above. The pad may be round in shape or have varying configurations. There would be a cut out, hole, or recess 40 of the center of the pad 39 which would be located underneath the dome 38 to accommodate the implanted port device 36. The recess or hole 40 would line up with the dome 38 on the back plate 37. The base diameter of the aperture/hole 40 would be approximately a nominal 1¼ inches. The diameter of the top of the hole 40 would be approximately a nominal 3/32 of an inch.

One embodiment of the device would be coated in fabric 41 so as to not irritate the skin 35. The fabric 41 would be attached to the device 32 with means 42 for securing such as an adhesive. The fabric 41 may have a variety of colors and styles for depending on the user 31 types. Colors and styles for boys could be different than colors and styles for girls.

There will be slots 44 cut into the back plate 37 and fabric coating 41 to allow for straps 33. The straps 33 may be made of soft elastic material that will not irritate the skin. Two quick release plastic clasps 34 would be utilized for ease of installation. They would be located in the front or in the back.

Figure 8:
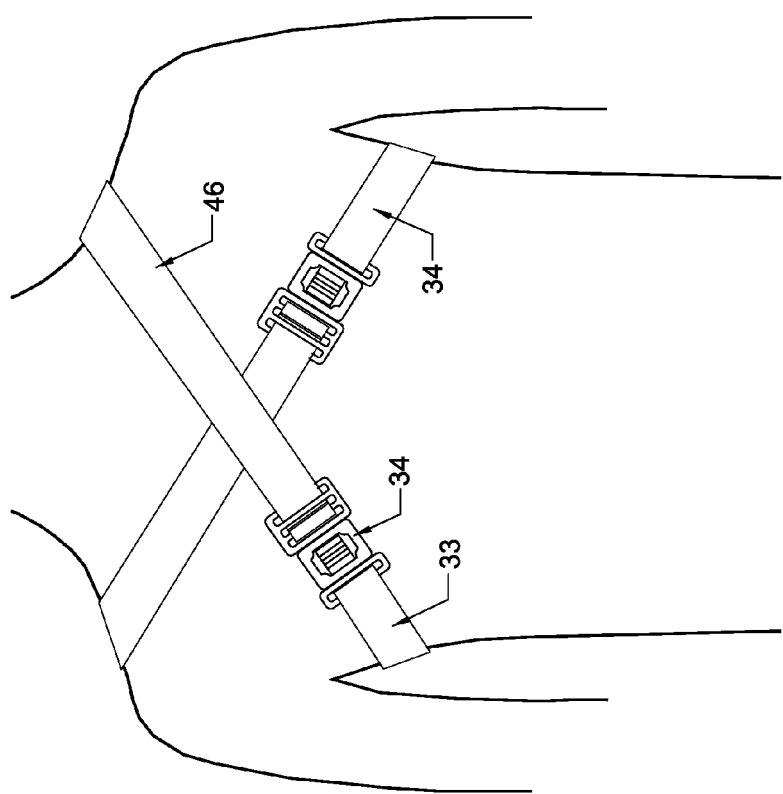
FIG. 8 is a back view of a second embodiment of the invention in use.

Another embodiment of the invention for girls and women would utilize a sports bra razor back type strap 46 as indicated on FIG. 8.

Figure 9:
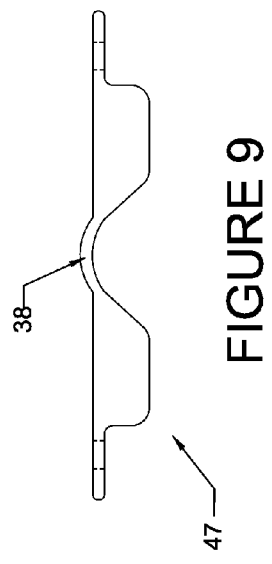
FIG. 9 is a cross section view of a second embodiment of the present invention.
Figure 10:
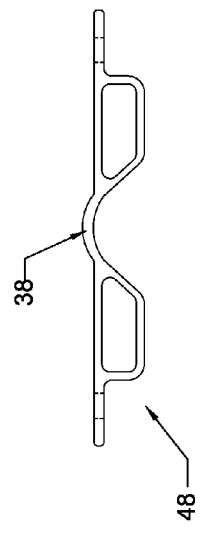
FIG. 10 is a cross section view of a third embodiment of the present invention.
Figure 11:
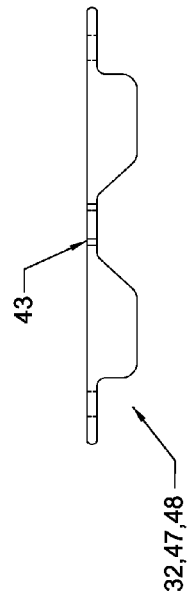
FIG. 11 is a cross section view of a fourth embodiment of the present invention.

Another embodiment of the invention consists of a single solid component 47 as seen on FIG. 9. This shows a single solid component (assembly or integral combination of pad 37 and plate 39 combination). This assembly/component 47 is constructed of molded plastic, vinyl, rigid foam or similar material. Other materials include molded plastic, rigid foam, urethane, nylon, natural rubber, synthetic rubber, and composite material. Still another embodiment of the invention consists of a similar single component/assembly of hollow construction 48 as seen on FIG. 10 made of the same materials as above.

FIG. 12 is a front view of the device 32 with an embodiment showing front clasps 34 for use with the device 32. These clasps are a means for securing and adjusting length of the strap 33 such as clasps, hooks, hook and loop devices [Velcro™) or equal. Here the clasps 34 are along the front of the user near the plate 37.

While the invention has been particularly shown and described with reference to preferred embodiments thereof, it would be understood by those skilled in the art that various changes in form and details may be made therein without departing from the spirit and scope of the invention.

OPERATION

The port protection device has been described in the above embodiments. The manner of how the device operates is described below. The port protection device is essentially comprised of a rigid back plate with a top and lower surface; a pad made of resilient material with a top surface and a lower surface, the top surface of the pad contiguously placed next to the lower surface of the back plate with a small gap at the junction of the contiguous surfaces and the lower surface of the pad next to a skin of a user; a means to secure the lower surface of the back plate to the top surface of the pad; a plurality of straps with a length long enough and able to wrap around a chest of the child; and a means to attach the plurality of straps to the back plate wherein the device is placed on the skin of the child directly over the port.

The port protection device 32 is intended to be easily and quickly installed and removed by a user 31. On the initial installation, the device is to be placed on the chest or abdomen directly over the implanted port device 36 and held in place by the child, while a parent extends the straps 33 to the child's back and connects the one or two strap ends with the clasps 34. The straps are then adjusted to ensure a tight but comfortable fit. On subsequent uses, the device 32 is simply held in place and the straps 33 clasped in the back. Removal simply takes place in reverse order.

The port protection device has the distinct benefits in that it:
Protects the child or user;
Protects the implanted device;
Promotes confidence of the user in physical activity;
Is light and durable;
Is easy to clean;
Is simple to attach around the body/chest of the child or user and requires no special tools;
Is available in universal sizes and requires no special customization to the user;
Is comprised of readily available materials;

With this description it is to be understood that the Port Protection Device 32 is not to be limited to only the disclosed embodiment of product. The features of the device are intended to cover various modifications and equivalent arrangements included within the spirit and scope of the description.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described above in the foregoing paragraphs.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

We claim:

1. A device for protecting an implanted port, which is capable of receiving medicine for an intravenous application, of an active child comprising:
   a. a rigid back plate with a top and a lower surface and with a plurality of slots essentially at the perimeter of the back plate;
   b. a pad made of resilient material with a top surface and a lower surface, the top surface of the pad contiguously placed next to the lower surface of the back plate with a small gap at the junction of the contiguous surfaces and the lower surface of the pad next to a skin of a user;
   c. a means to secure the lower surface of the back plate to the top surface of the pad;
   d. a plurality of straps with a length long enough and able to wrap around a chest and shoulders of the active child; and
   e. a means to attach the plurality of straps threading each strap through the slots essentially at the perimeter of the back plate to the back plate of the device wherein the plurality of the straps extend from the perimeter of the back plate and wherein the device is placed on the skin of the active child directly over the implanted port and promotes confidence of the active child in physical activities.

2. The rigid material in claim 1 wherein the material is selected from the group consisting of molded plastic, rigid urethane, nylon, sheet plastic, rigid pressed cardboard, thin gaged metal, and rigid composite material.

3. The back plate of claim 1 wherein the device is further comprised of a raised dome formed integrally into the center of the back plate of the device.

4. The pad of claim 1 wherein the resilient material comprising the pad is a shock absorbing material.

5. The shock absorbing material in claim 4 wherein the material is selected from the group consisting of molded plastic, rigid foam, urethane, nylon, natural rubber, synthetic rubber, composite material, foam, Poron® urethane, and silicone gel.

6. The pad of claim 4 wherein there is a recess for surrounding the implanted ports and the recess is approximately in and near the center of the pad.

7. The plurality of the straps of claim 1 wherein the long straps are comprised with a means to adjust the length of the strap.

8. The device in claim 1 wherein the back plate, the means to secure the plate to the pad and the pad comprise a single piece assembly wherein the assembly contains a centrally located recess.

9. The single piece assembly of claim 8 wherein the assembly is made of a solid piece of material selected from the group consisting of molded plastic, rigid foam, urethane, nylon, natural rubber, synthetic rubber, and composite material.

10. The single piece assembly of claim 8 wherein the assembly is hollow.

11. The device of claim 1 wherein the a back plate, the pad, and the means to secure the back plate to the pad assembly is further comprised with a fabric which encases the device
   wherein the fabric can further protect the skin of the active child.

12. A device for protecting an implanted port of a child user comprising:
   a. a back plate with a raised dome, with a top and a lower surface, and with a plurality of slots essentially at the perimeter of the back plate;
   b. a rigid pad with a centrally located recess and with a top surface and a lower surface, the top surface of the pad contiguously placed next to the lower surface of the back plate with a small gap at the junction of the contiguous surfaces and the lower surface of the pad next to a skin of a user;
   c. a means to secure the lower surface of the back plate to the top surface of the pad;
   d. a plurality of straps with a length long enough and able to wrap around a chest and shoulders of the child;
   e. a means to attach the plurality of straps to the back plate at the slots essentially at the perimeter of the back plate; and
   f. a means to adjust the length of the straps
   wherein the plurality of the straps extend from the perimeter of the back plate and wherein the device is placed on the skin of the active child directly over the implanted port and promotes confidence of the active child in physical activities.

13. The device of claim 12 wherein the a back plate, the rigid pad, and the means to secure the back plate to the rigid pad assembly are further comprised with a fabric which encases the device
   wherein the fabric can further protect the skin of the active child.

* * * * *